US009820630B2

(12) United States Patent
Tomita (10) Patent No.: US 9,820,630 B2
(45) Date of Patent: Nov. 21, 2017

(54) LEAK TESTER AND ENDOSCOPE REPROCESSOR

(71) Applicant: OLYMPUS CORPORATION, Tokyo (JP)

(72) Inventor: Masahiko Tomita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/283,848

(22) Filed: Oct. 3, 2016

(65) Prior Publication Data

US 2017/0020367 A1 Jan. 26, 2017

Related U.S. Application Data

(63) Continuation of application No. PCT/JP2015/079178, filed on Oct. 15, 2015.

(30) Foreign Application Priority Data

Jan. 26, 2015 (JP) .................................. 2015-012592

(51) Int. Cl.
  *A61B 1/00* (2006.01)
  *A61B 1/12* (2006.01)
  (Continued)

(52) U.S. Cl.
  CPC ............ *A61B 1/00057* (2013.01); *A61B 1/00* (2013.01); *A61B 1/12* (2013.01); *G01M 3/26* (2013.01);
  (Continued)

(58) Field of Classification Search
  CPC .............................. G01M 3/26; A61B 1/00057
  See application file for complete search history.

(56) References Cited

U.S. PATENT DOCUMENTS

| 5,375,453 A * | 12/1994 | Rudd ..................... G01M 3/223 374/47 |
| 2001/0015091 A1 * | 8/2001 | Messmann .......... G01M 3/2846 73/37 |

(Continued)

FOREIGN PATENT DOCUMENTS

| CN | 1954768 A | 5/2007 |
| EP | 1666864 A1 | 6/2006 |

(Continued)

OTHER PUBLICATIONS

International Search Report dated Dec. 28, 2015 issued in PCT/JP2015/079178.

Primary Examiner — Paul West
(74) Attorney, Agent, or Firm — Scully, Scott, Murphy & Presser, P.C.

(57) ABSTRACT

When an air supply conduit is connected to an empty space portion inside an endoscope and air is fed to the empty space portion to perform a leak determination based on a change in the internal pressure of the endoscope which is caused by the air, a surface temperature of the endoscope that is measured by a temperature measurement portion is maintained at a temperature at the time that the leak determination starts, through energy supply control that irradiates far infrared rays onto a surface of the endoscope from a far-infrared ray irradiation portion.

8 Claims, 10 Drawing Sheets

(51) Int. Cl.
*G02B 23/24* (2006.01)
*G01M 3/26* (2006.01)

(52) U.S. Cl.
CPC ......... *G02B 23/24* (2013.01); *G02B 23/2476* (2013.01)

(56) References Cited

U.S. PATENT DOCUMENTS

| | | |
|---|---|---|
| 2006/0196250 A1 | 9/2006 | Gocho |
| 2014/0238110 A1 | 8/2014 | Williams |

FOREIGN PATENT DOCUMENTS

| | | |
|---|---|---|
| EP | 2772220 A1 | 9/2014 |
| JP | H07-273875 A | 6/1995 |
| JP | 2000-306876 A | 11/2000 |
| JP | 2003-186551 A | 7/2003 |
| JP | 2005-091042 A | 4/2005 |
| JP | 2007-273875 A | 10/2007 |
| JP | 2011-191157 A | 9/2011 |
| JP | 2014-161737 A | 9/2014 |

* cited by examiner

LEAK TESTER AND ENDOSCOPE REPROCESSOR

CROSS REFERENCE TO RELATED APPLICATION

This application is a continuation application of PCT/JP2015/079178 filed on Oct. 15, 2015 and claims benefit of Japanese Application No. 2015-012592 filed in Japan on Jan. 26, 2015, the entire contents of which are incorporated herein by this reference.

BACKGROUND OF INVENTION

1. Field of the Invention

The present invention relates to a leak tester that injects pressurized air into an object that requires a sealing property and performs leak determination based on a change in the internal pressure after injecting the pressurized air, and also relates to an endoscope reprocessor.

2. Description of the Related Art

For example, endoscopes that are used in the medical field are subjected to a cleaning and disinfecting treatment after use to prevent infectious disease and the like. Since such kind of cleaning/disinfecting treatment generally uses a liquid, in a case where a sealing property of an endoscope is not maintained due to damage to an outer covering or due to looseness of a connection portion or the like, there is a risk of a liquid such as water or a cleaning liquid entering into the endoscope and causing a failure in an electrical system or the like such as an image pickup device. Therefore, a leak test needs to be carried out before performing a cleaning/disinfecting treatment on an endoscope.

As a method for automating leak determination on such an object that requires a sealing property, a technology is known which injects pressurized air into the object and performs leak determination by measuring a pressure change after allowing the object to stand for a fixed time period. In this case, after the pressurized air is injected, the internal pressure of the object changes not only when the pressurized air leaks but also when the pressurized air undergoes thermal contraction or thermal expansion due to a temperature change when the object is affected by the ambient temperature.

As technology for eliminating the effect of such disturbance and improving the accuracy of leak determination, for example, Japanese Patent Application Laid-Open Publication No. 2003-186551 discloses a technology that performs leak determination after controlling the temperature of an examination object by means of heated or cooled water so as to track the ambient temperature.

SUMMARY OF THE INVENTION

A leak tester according to one aspect of the present invention includes: a connection portion that is communicably connected to inside of an object; an air feeding portion configured to feed a gas into the object through the connection portion; an internal pressure measurement portion configured to measure an internal pressure of the object; a temperature measurement portion configured to measure a surface temperature of the object; a constant temperature portion configured to supply energy toward a surface of the object; and a control portion that is connected to the air feeding portion, the internal pressure measurement portion, the temperature measurement portion, and the constant temperature portion, and is configured to set as a target temperature a surface temperature of the object that is measured by the temperature measurement portion before driving of the internal pressure measurement portion and the air feeding portion, and to control the constant temperature portion so that the constant temperature portion causes a change in the surface temperature of the object to be a temperature within a predetermined range from the target temperature at least during driving of the internal pressure measurement portion.

Further, an endoscope reprocessor according to one aspect of the present invention includes a leak tester including: a connection portion that is communicably connected to inside of an object; an air feeding portion configured to feed a gas into the object through the connection portion; an internal pressure measurement portion configured to measure an internal pressure of the object; a temperature measurement portion configured to measure a surface temperature of the object; a constant temperature portion configured to supply energy toward a surface of the object; a control portion that is connected to the air feeding portion, the internal pressure measurement portion, the temperature measurement portion, and the constant temperature portion, and is configured to set as a target temperature a surface temperature of the object that is measured by the temperature measurement portion before driving of the internal pressure measurement portion and the air feeding portion, and to control the constant temperature portion so that the constant temperature portion causes a change in the surface temperature of the object to be a temperature within a predetermined range from the target temperature at least during driving of the internal pressure measurement portion; and a housing portion configured to house the object, wherein the constant temperature portion controls a temperature of a gas inside the housing portion to a same temperature as the surface temperature of the object at a predetermined timing when the object is housed in the housing portion or to a temperature in a predetermined range obtained by adding and subtracting a predetermined temperature to and from the surface temperature, the leak tester takes an endoscope as the object, the connection portion includes an endoscope connection portion that communicates with inside of the endoscope, and the housing portion is a treatment tank configured to house the endoscope.

DETAILED DESCRIPTION OF THE PREFERRED EMBODIMENT(S)

Hereunder, modes of the present invention are described with reference to the accompanying drawings. Drawings relating to a first embodiment of the present invention include FIG. 1 which is a block diagram illustrating a basic configuration of a leak tester that is connected to an endoscope, and FIG. 2 which is a flowchart illustrating a leak determination routine with respect to an endoscope.

Figure 1:
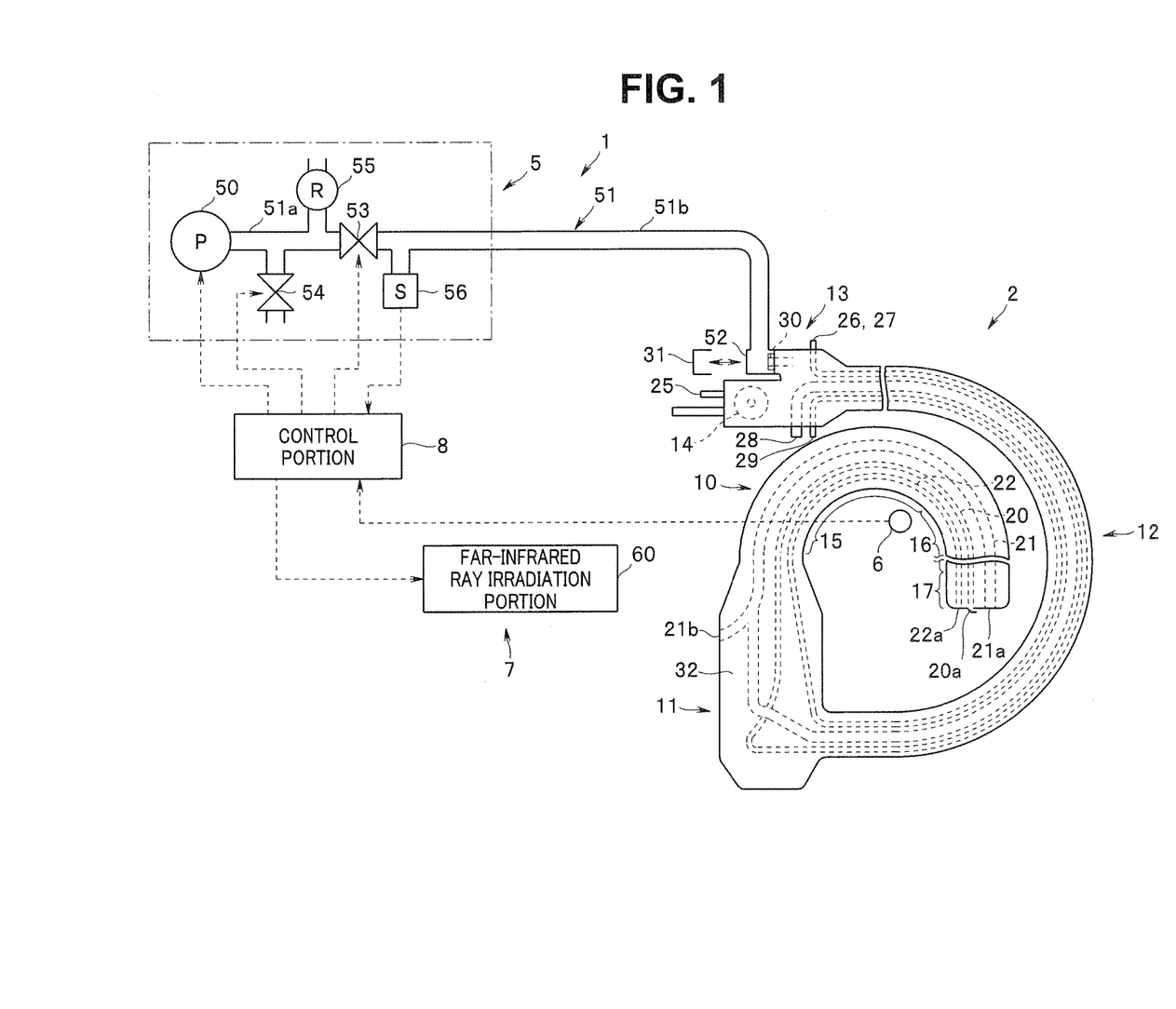
FIG. 1 is a block diagram illustrating a basic configuration of a leak tester that is connected to an endoscope according to a first embodiment of the present invention.

A leak tester 1 of the present embodiment that is illustrated in FIG. 1 is, for example, a leak tester that performs leak determination with respect to an endoscope 2 for medical use as an object. The leak tester 1 includes a leak tester main body 5, a temperature measurement portion 6 that measures a surface temperature of the endoscope 2, a constant temperature portion 7 configured to maintain a surface temperature T of the endoscope 2 within a predetermined range, and a control portion 8 configured to perform control of the leak tester main body 5 and the constant temperature portion 7.

The endoscope 2 as a leak determination object includes: an elongated insertion portion 10 that has flexibility; an operation portion 11 that is connected to a proximal end side of the insertion portion 10; a connecting cord (universal cord) 12 that has flexibility and is extended from a side part of the operation portion 11; a connector portion 13 which is provided at an end portion of the connecting cord 12 and which is detachably connected to an unshown light source apparatus; and an electrical connector portion 14 which is provided at a side part of the connector portion 13, and is detachably connectable to an unshown video processor through a signal cable.

The insertion portion 10 includes: a flexible tube portion 15 which is flexible and soft; a bending portion 16 which is provided on a distal end side of the flexible tube portion 15 and which can be bent by an operation of the operation portion 11; and a distal end portion 17 which is provided on a distal end side of the bending portion 16 and in which an unshown observation optical system and illumination optical system and the like are provided.

In the distal end portion 17 is provided an air/water feeding nozzle 20a for ejecting a cleaning liquid or a gas supplied from an air/water feeding tube 20 toward an optical member on an outer surface of an unshown observation optical system. Also provided in the distal end portion 17 is a suction port 21a which is an opening on a distal end side of a treatment instrument channel 21 that is used for inserting a treatment instrument through the suction port 21a and for performing suction of in-vivo fluids. Further provided in the distal end portion 17 is a liquid feeding port 22a for ejecting a liquid that is supplied from a liquid feeding tube for forward water feeding 22 toward an observation object.

In the operation portion 11 are provided an air/water feeding operation button configured to perform an air feeding operation and a water feeding operation, a suction operation button configured to perform a suction operation, a bending operation knob configured to perform a bending operation of the bending portion 16, a plurality of remote switches configured to perform remote operation of a video processor (none of which are illustrated in the drawings) and a treatment instrument insertion port 21b that is an opening which communicates with the treatment instrument channel 21.

Provided in the connector portion 13 are a gas supply pipe sleeve 25 that is detachably connected to an air supply source which is built in the light source apparatus, and a water feeding tank pressurizing pipe sleeve 26 and a liquid supply pipe sleeve 27 which are detachably connected to an unshown water feed tank as a liquid supply source are provided in the connector portion 13. A suction pipe sleeve 28 that is connected to an unshown suction source configured to perform suction through the suction port 21a is provided on a rear side of the water feeding tank pressurizing pipe sleeve 26 and the liquid supply pipe sleeve 27. Further, in the vicinity of the suction pipe sleeve 28, an injection pipe sleeve 29 that is connected to unshown water feeding means configured to perform water feeding through the liquid feeding port 22a is provided.

In addition, a ventilation portion 30 is provided in the connector portion 13. The ventilation portion 30 is a communicating hole configured to allow communication between the endoscope exterior and an empty space portion 32 of a region which is blocked off in a watertight manner between the outer surface of a conduit that is inserted through the inside of the endoscope 2 and an exterior member (outer covering portion) of the endoscope 2. A waterproof cap 31 is detachably mounted on the ventilation portion 30, and by this means the empty space portion 32 is blocked off in a watertight manner when using the endoscope 2 and the like.

Note that, because the endoscope 2 configured as described above is heated by heat sources such as the body temperature of the subject, heat emitted from electrical components, and illuminating light and the like, normally the temperature of the endoscope 2 immediately after use is higher than the ambient temperature.

The leak tester main body 5 includes an air pump 50 as an air feeding portion. The air pump 50 is a diaphragm-type air pump, for example. One end side of an air supply conduit 51 is connected to a discharge port of the air pump 50.

On the other hand, a connector 52 as a connection portion is provided on the other end side of the air supply conduit 51. The connector 52 is configured to be detachably attachable to the ventilation portion 30 provided in the connector portion 13 of the endoscope 2. By connecting the connector 52 to the ventilation portion 30 formed in the waterproof cap 31, it is enabled to cause the air supply conduit 51 to communicate with the inside (empty space portion 32) of the endoscope 2.

Further, an opening/closing valve 53 is interposed partway along the air supply conduit 51. The opening/closing valve 53 performs an opening or closing operation in accordance with a control signal from the control portion 8. When the opening/closing valve 53 is in an open state, the opening/closing valve 53 allows communication between an upstream-side conduit portion 51a (that is, a conduit portion on the air pump 50 side) and a downstream-side conduit portion 51*b* (that is, a conduit portion on the connector 52 side) of the air supply conduit 51. This allows introducing a gas from the air pump 50 into the empty space portion 32 of the endoscope 2. The type of gas is not particularly limited, and for example, air can be used. The gas may also be compressed gas.

In contrast, when the opening/closing valve 53 is in a closed state, the upstream-side conduit portion 51*a* and the downstream-side conduit portion 51*b* of the air supply conduit 51 are cut off from each other (on the air pump 50 side). This allows the downstream-side conduit portion 51*b* of the air supply conduit 51 to form an integrated closed space with the empty space portion 32 of the endoscope 2.

Further, an atmosphere release valve 54 and a relief valve 55 are provided in the upstream-side conduit portion 51*a* of the air supply conduit 51. The atmosphere release valve 54 performs an opening or closing operation in accordance with a control signal from the control portion 8. In an open state, the atmosphere release valve 54 opens the upstream-side conduit portion 51*a* to the atmosphere. The relief valve 55 mechanically performs an opening operation when the internal conduit pressure of the upstream-side conduit portion 51*a* enters an overpressure state that is equal to or greater than a previously set pressure, and can thus open the upstream-side conduit portion 51*a* to the atmosphere.

A gauge pressure sensor 56 configured to measure the internal conduit pressure of the air supply conduit 51 is provided in the downstream-side conduit portion 51*b* of the air supply conduit 51. When the opening/closing valve 53 is closed and a closed space is formed by the downstream-side conduit portion 51*b* and the empty space portion 32, the gauge pressure sensor 56 can act as an internal pressure measurement portion that measures the internal pressure of the endoscope 2 that is the object of a leak determination operation.

The temperature measurement portion 6 is, for example, configured by a temperature sensor that includes a thermocouple or a resistance temperature sensor. The temperature measurement portion 6 can measure the surface temperature T of the endoscope 2 that is the object by being disposed in contact with the surface of the endoscope 2. Alternatively, the temperature measurement portion 6 can indirectly measure the surface temperature T by being disposed in a non-contacting state in the vicinity of the endoscope 2, with a predetermined correction being applied to the measurement result. Further, in a case where a temperature sensor is incorporated inside the endoscope 2, a configuration can be adopted that uses the incorporated temperature sensor as the temperature measurement portion 6 and estimates the surface temperature based on the internal temperature of the endoscope 2 that is measured. Alternatively, a configuration can be adopted in which the temperature measurement portion 6 is configured by a non-contact temperature sensor such as an infrared sensor, and the surface temperature T is measured by image processing by use of thermography.

The constant temperature portion 7, for example, is configured by a far-infrared ray irradiation portion 60 that is capable of supplying far infrared rays onto the surface of the endoscope 2. In this case, far infrared rays are used as the aforementioned energy, and the temperature of the object can be prevented from decreasing by irradiating far infrared rays onto the object.

The amount of far infrared rays irradiated by the far-infrared ray irradiation portion 60 is controlled, for example, by the proportion of an "on" time period in each cycle of a supplied alternating current being controlled by phase control at the control portion 8. By the irradiated amount of far infrared rays being controlled in this way, the far-infrared ray irradiation portion 60 is enabled to keep the surface temperature of the endoscope 2 within a predetermined range.

Figure 2:
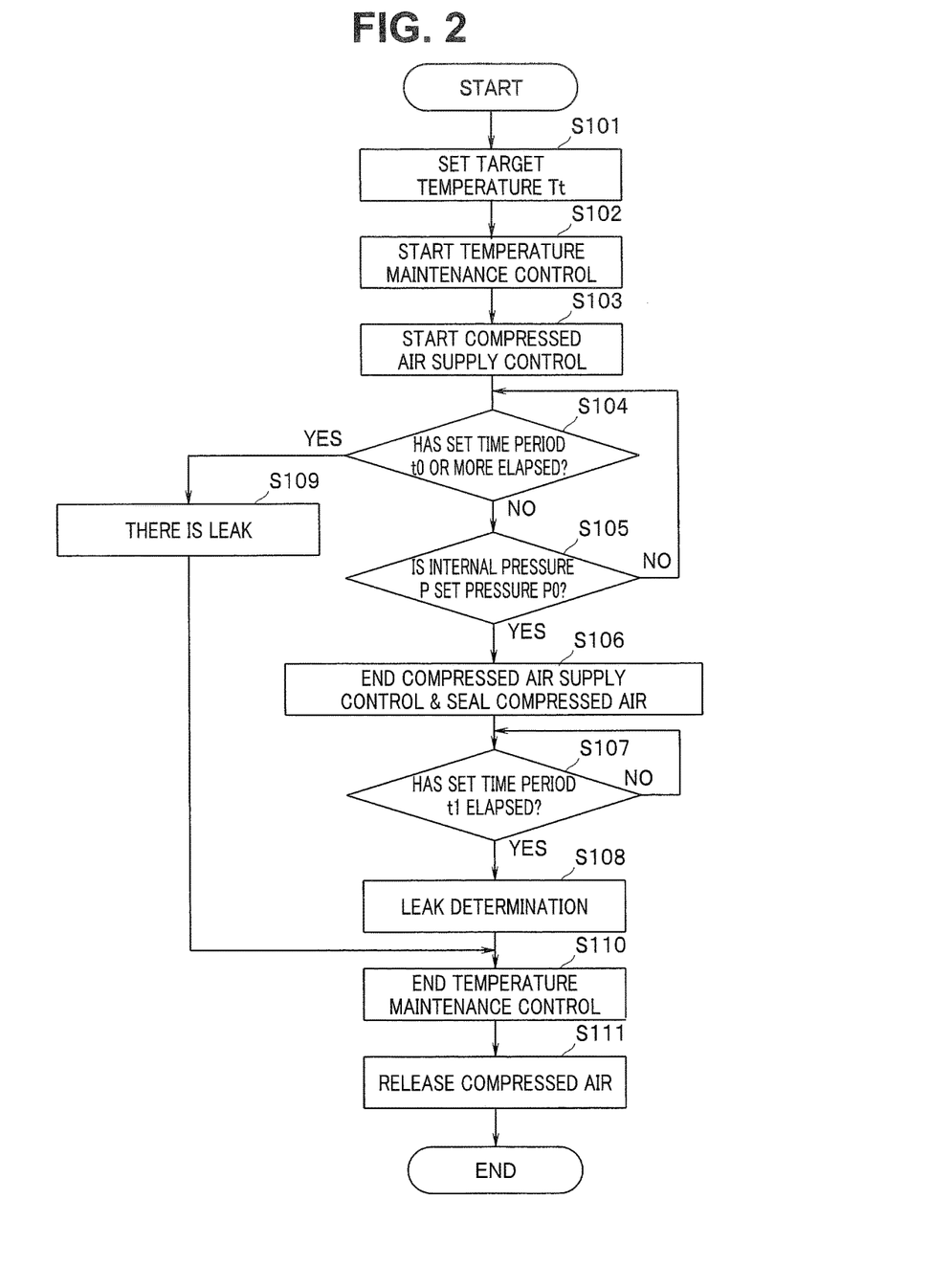
FIG. 2 is a flowchart illustrating a leak determination routine with respect to an endoscope according to the first embodiment of the present invention.

Next, a process to determine a leak with respect to the endoscope 2 that is executed by the control portion 8 will be described in accordance with a flowchart illustrating a leak determination routine that is shown in FIG. 2. This routine starts after the connector 52 of the leak tester main body 5 is connected to the ventilation portion 30 of the endoscope 2, and the endoscope 2 is set at a preset position with respect to the temperature measurement portion 6 and the constant temperature portion 7. Note that, since the endoscope 2 that is the object of the present embodiment is long, for example, the endoscope 2 is set in the leak tester 1 in a state in which the endoscope 2 is wound in an annular shape as shown in FIG. 1.

When the routine starts, first, in step S101, the control portion 8 sets the surface temperature T of the endoscope 2 that is currently (that is, immediately after the leak determination control starts) being measured by the temperature measurement portion 6 as a target temperature Tt.

Next, in step S102, the control portion 8 starts temperature maintenance control for maintaining the surface temperature T of the endoscope 2 at the target temperature Tt. The temperature maintenance control is performed, for example, by performing feedback control of a power supply amount to the far-infrared ray irradiation portion 60 (that is, the irradiation amount of far infrared rays with respect to the endoscope 2) based on the target temperature Tt and the current surface temperature T.

Next, in step S103, the control portion 8 starts to control the supply of air into the endoscope 2 by the leak tester main body 5. That is, the control portion 8 performs control to open the opening/closing valve 53, and also performs control to close the atmosphere release valve 54, and thereafter starts the supply of air into the endoscope 2 by driving the air pump 50.

Next, upon the processing proceeding to step S104 from step S103, the control portion 8 checks whether or not a set time period t0 or more has elapsed since the supply of air started. Here, the set time period t0 is set, for example, to a time period which is sufficient for the internal pressure P of the endoscope 2 to be increased to a previously set pressure P0 by the supply of air from the air pump 50.

If the control portion 8 determines in step S104 that the elapsed time period since the supply of air started is equal to or greater than the set time period t0, the control portion 8 proceeds to step S109 in which the control portion 8 determines that a leak has clearly occurred in the endoscope 2, and thereafter proceeds to step S110.

In contrast, in a case where the control portion 8 determines in step S104 that the elapsed time period since the supply of air started is less than the set time period t0, the control portion 8 proceeds to step S105 to check whether or not the internal pressure P of the endoscope 2 that is measured by the gauge pressure sensor 56 has reached the set pressure P0.

If the control portion 8 determines in step S105 that the internal pressure P of the endoscope 2 is less than the set pressure P0, the control portion 8 returns to step S104.

In contrast, if the control portion 8 determines in step S105 that the internal pressure P of the endoscope 2 has reached the set pressure P0, the control portion 8 proceeds to step S106. In step S106, the control portion 8 stops the air pump 50 and ends control of the supply of air, and also controls to close the control valve 53 and seal air inside the empty space portion 32 of the endoscope 2 and within the downstream-side conduit portion 51b of the air supply conduit 51.

Next, the control portion 8 proceeds to step S107 to determine whether or not a previously set leak determination time period t1 has elapsed since sealing the air as described above.

If it is determined in step S107 that the leak determination time period t1 has not yet elapsed, the control portion 8 waits in that state.

In contrast, if it is determined in step S107 that the leak determination time period t1 has elapsed, the control portion 8 proceeds to step S108. In step S108, the control portion 8 determines whether or not a leak occurs in the endoscope 2 based on a change in the internal pressure P of the endoscope 2 from the time that the air was sealed until the time that the leak determination time period t1 elapsed. Thereafter, the control portion 8 proceeds to step S110.

Upon proceeding to step 110 from step S108 or step S109, the control portion 8 stops the supply of power to the far-infrared ray irradiation portion 60 to end the temperature maintenance control for the endoscope 2. Next, in step S111, the control portion 8 controls to open the control valve 53 and the atmosphere release valve 54 to thereby release air inside the endoscope 2 into the atmosphere, and thereafter ends the routine.

According to the embodiment, when the air supply conduit 51 is connected to the empty space portion 32 inside the endoscope 2 and air is fed to the empty space portion 32 and a leak determination is performed based on a change in the internal pressure of the endoscope 2 caused by the fed air, by maintaining the surface temperature T of the endoscope 2 which is measured by the temperature measurement portion 6 at the temperature Tt at the time that the leak determination starts (that is, by keeping a change in the surface temperature T of the endoscope 2 within a predetermined range that is based on the target temperature Tt) through energy supply control which irradiates far infrared rays onto the surface of the endoscope 2 from the far-infrared ray irradiation portion 60, even in a case where the temperature T of the endoscope 2 is different from the ambient temperature, it is enabled to prevent an erroneous determination due to a change in the internal pressure caused by thermal contraction of air or the like and to accurately perform automatic leak determination in a short time period.

That is, when performing a leak determination, the influence of a disturbance caused by a temperature difference between the temperature of the endoscope 2 and the ambient temperature can be eliminated by keeping the temperature of the endoscope 2 itself constant by maintaining the surface temperature T of the endoscope 2 and without causing the temperature of the endoscope 2 to track the ambient temperature. It is thus enabled to accurately perform an automatic leak determination in a short time period without requiring the time period to cause the temperature of the endoscope 2 to track the ambient temperature. In other words, the influence of the ambient temperature on the endoscope 2 can be precisely eliminated and an automatic leak determination can be accurately performed in a short time period by suppressing a change in the temperature of the endoscope 2 itself by managing the surface temperature T, by focusing on the fact that the endoscope 2 that has a high temperature immediately after use is cooled over a predetermined time period mainly by heat exchange on the surface of the endoscope 2 that contacts the external air.

In this case, in particular, in the endoscope 2 in which the internal empty space portion 32 is formed in the shape of a long and narrow tube, it is difficult to circulate air or the like for cooling inside the empty space portion 32 and therefore a long time period is required to cool the temperature of the endoscope 2 itself to the ambient temperature. However, since the leak tester 1 of the present embodiment performs a leak determination while maintaining the temperature of the endoscope 2 and not causing the temperature of the endoscope 2 to track the ambient temperature, an automatic leak determination can be started in a short time period and, furthermore, high determination accuracy can be secured.

Figure 3:
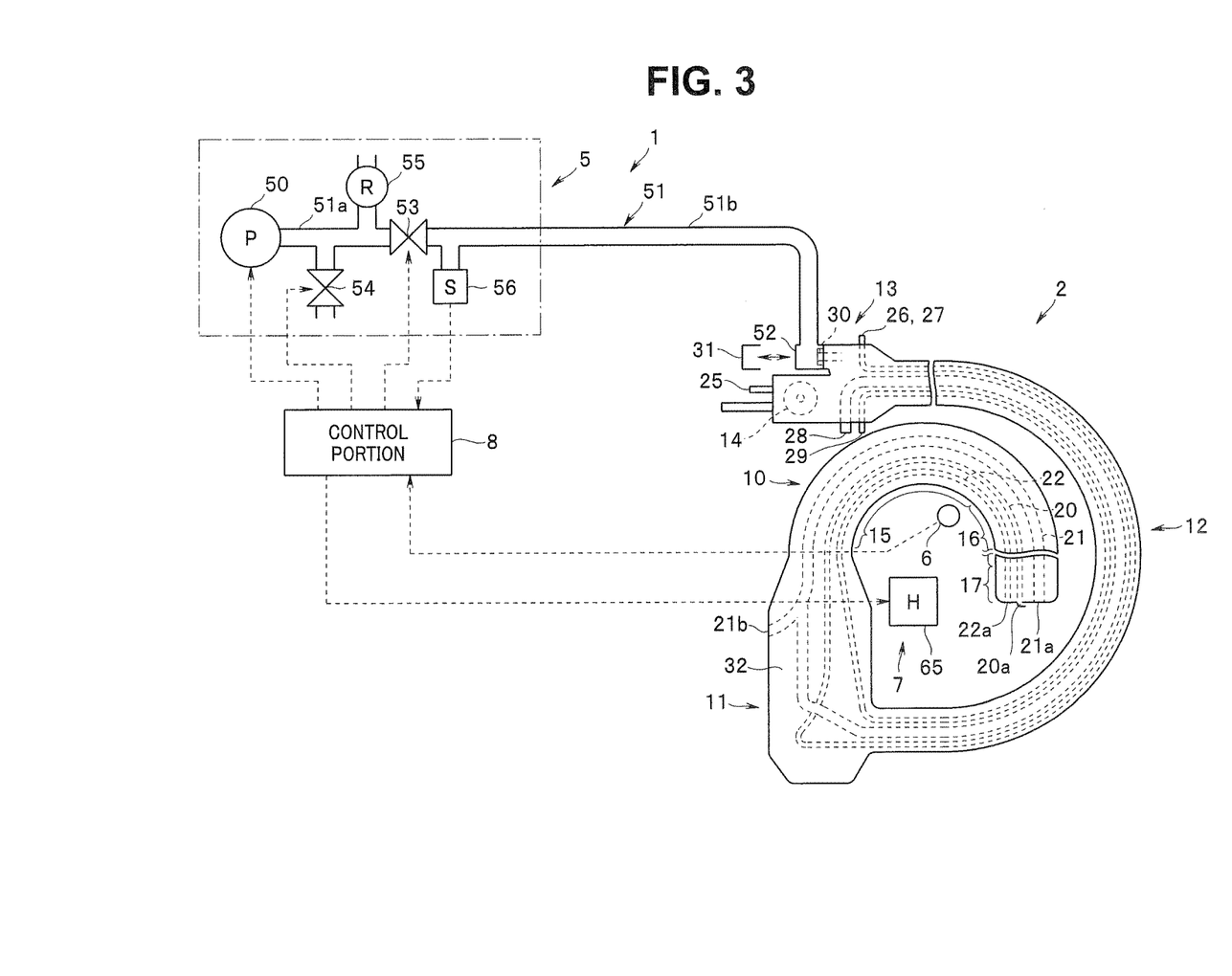
FIG. 3 is a block diagram illustrating a basic configuration of a leak tester that is connected to an endoscope according to a second embodiment of the present invention.

Next, FIG. 3 is a block diagram illustrating a basic configuration of a leak tester connected to an endoscope that relates to a second embodiment of the present invention. Note that the main difference between the present embodiment and the above-described first embodiment is that while in the first embodiment a configuration is described in which the surface temperature T of the endoscope 2 is maintained at the target temperature Tt by directly heating the surface of the endoscope 2 by irradiation of light energy that is typified by far infrared rays, in the present embodiment a configuration is adopted that maintains the surface temperature T at the target temperature Tt by heating the atmosphere around the endoscope 2 or the like. Note that components which are the same as in the above-described first embodiment are denoted by the same reference numerals and descriptions of such components are omitted.

As shown in FIG. 3, the constant temperature portion 7 of the present embodiment is, for example, constituted by a heater 65 as a heat source portion that is capable of heating the atmosphere around the endoscope 2. In the present embodiment, the heater 65 is, for example, constituted by a heating wire heater, and can be disposed in the vicinity of the endoscope 2.

Similarly to the above-described first embodiment, the heater 65 is subjected to feedback control by the control portion 8 based on the target temperature Tt and the surface temperature T of the endoscope 2. By this means, it is possible for the heater 65 to heat the atmosphere around the endoscope 2 and supply thermal energy to the surface of the endoscope 2.

In a case where the leak tester itself does not have an air blowing portion as shown in a modification described hereunder, it is preferable to adopt an arrangement such that heated atmospheric air can quickly reach the endoscope 2.

For example, preferably an endoscope housing portion of the leak tester itself or a housing portion that houses the leak tester and the endoscope has a shape that facilitates convection of gas.

As another example, preferably a leak tester and an air blowing portion that causes gas convection to occur are used in combination.

As a further example, preferably a heat source portion is disposed in the vicinity of the endoscope.

According to such a configuration, similar advantageous effects as in the above-described first embodiment can be achieved. In the present embodiment that supplies energy through the atmosphere to the surface of the endoscope 2, various modifications are possible, as illustrated in FIG. 4 to FIG. 8, for example.

Figure 4:
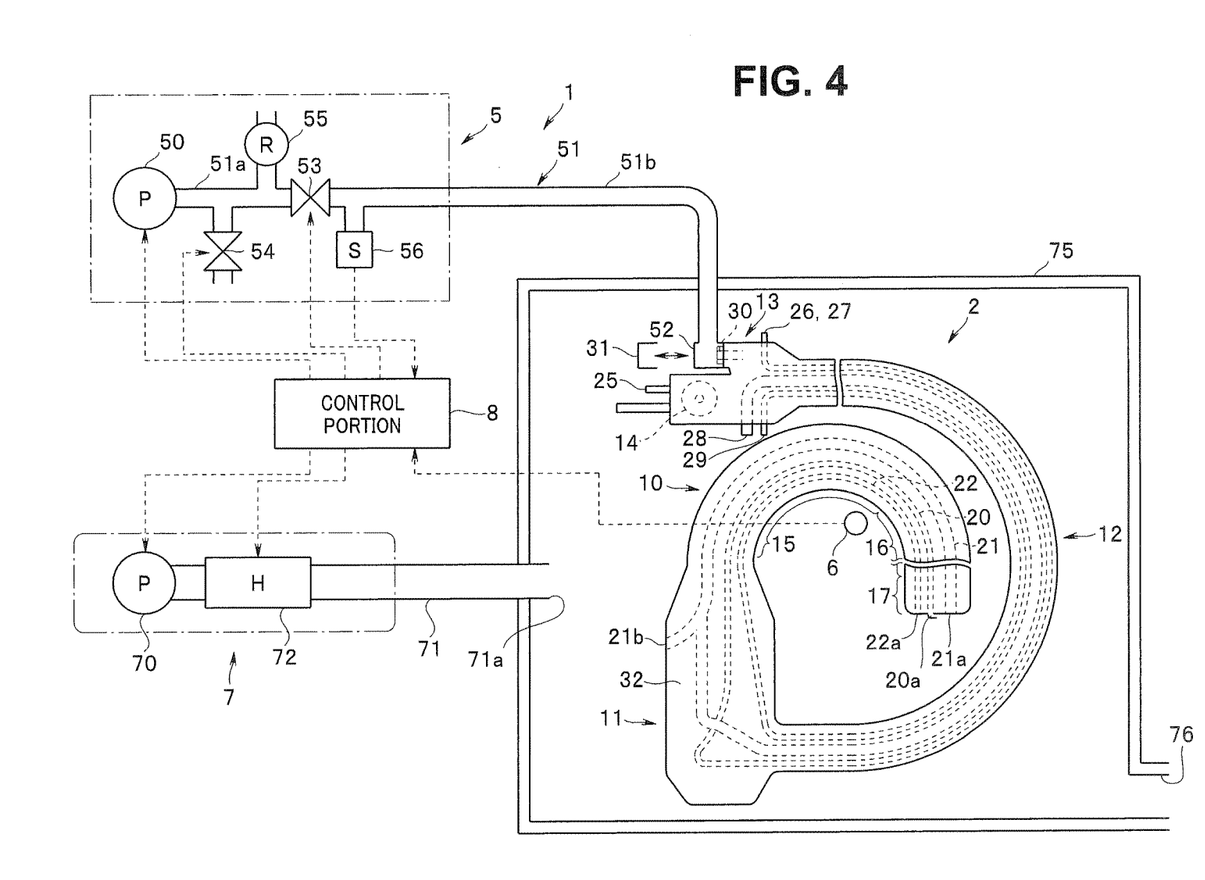
FIG. 4 is a block diagram illustrating a basic configuration of a leak tester that is connected to an endoscope according to a first modification of the second embodiment of the present invention.

FIG. 4 is a block diagram illustrating a basic configuration of a leak tester connected to an endoscope that relates to a first modification of the present embodiment.

As shown in FIG. 4, in the present modification, the constant temperature portion 7 includes an air feeding pump 70 as an air blowing portion configured to blow air toward the endoscope 2, an air feed passage 71 that is connected to the air feeding pump 70, and a heater 72 as a heat source portion that is interposed partway along the air feed passage 71. Further, in the constant temperature portion 7, by disposing an air blowing port 71a that opens at a downstream end of the air feed passage 71 so as to be directed at the endoscope 2, it is enabled to supply air that is heated by the heater 72 as atmospheric air around the endoscope 2.

It is desirable that the leak tester 1 has a housing portion 75 for housing the endoscope 2 in order to accurately manage the ambient temperature around the endoscope 2. In this case, the downstream side of the air feed passage 71 is connected to the housing portion 75, and the air blowing port 71a that opens at the downstream end of the air feed passage 71 is disposed so as to face the endoscope 2 inside the housing portion 75.

Further, an exhaust port 76 for discharging excess air that results from blowing of air from the constant temperature portion 7 is provided in the housing portion 75. In the present modification in which air that is heated by the constant temperature portion 7 is supplied, it is desirable that the exhaust port 76 is provided at a lower part of the housing portion 75, and by configuring the housing portion 75 in this manner, warm air that is supplied from the constant temperature portion 7 can be efficiently accumulated inside the housing portion 75.

Note that in a configuration that includes the housing portion 75 in this manner, it is desirable to adopt, as the target temperature Tt, a temperature that is the same as a temperature measured by the temperature measurement portion 6 at a predetermined timing when the endoscope 2 is housed in the housing portion 75 (for example, a timing immediately after the endoscope 2 is housed in the housing portion 75), or a temperature that is within a predetermined range obtained by adding and subtracting a predetermined temperature to and from the measured temperature.

Figure 5:
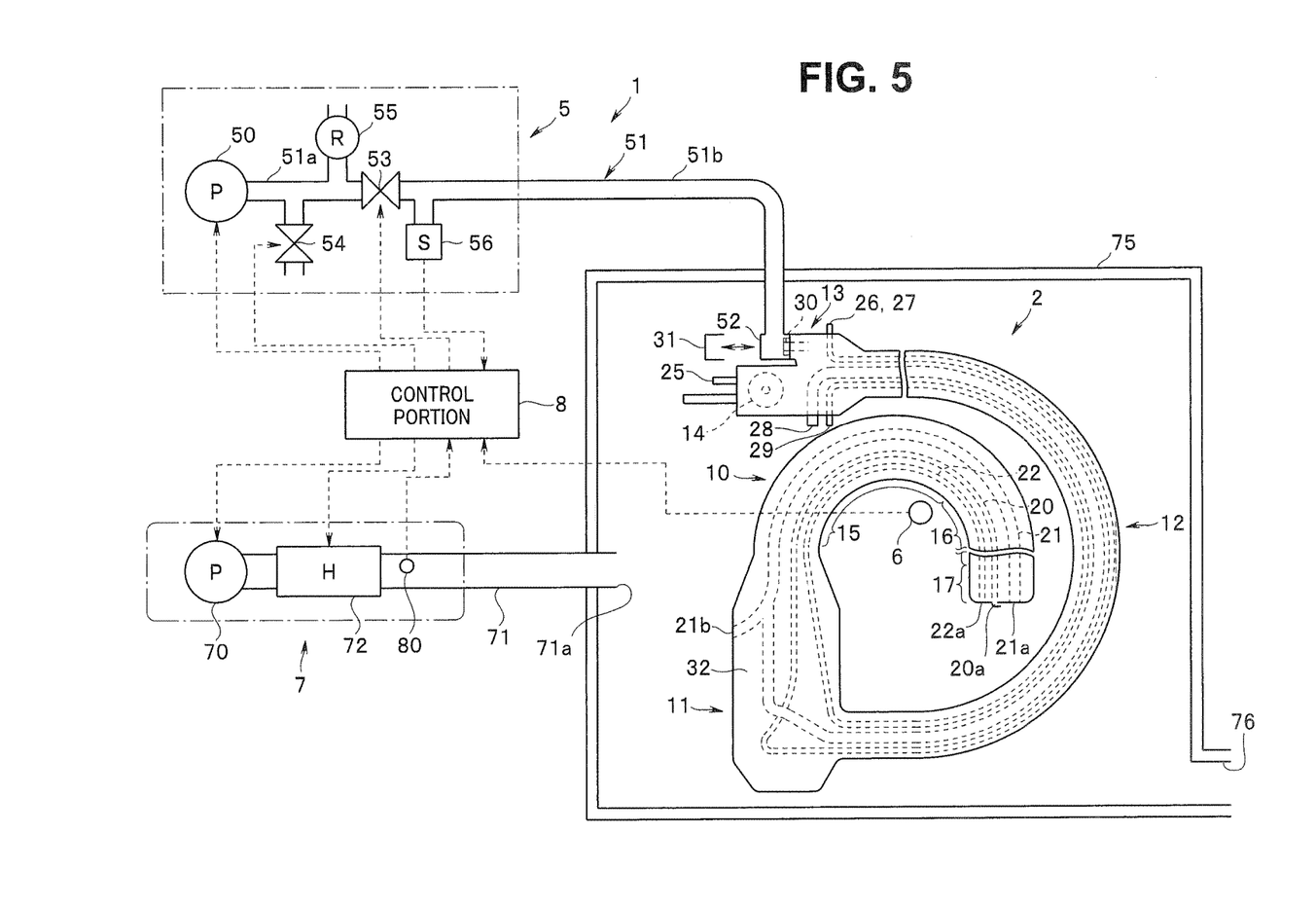
FIG. 5 is a block diagram illustrating a basic configuration of a leak tester that is connected to an endoscope according to a second modification of the second embodiment of the present invention.

Next, FIG. 5 is a block diagram illustrating a basic configuration of a leak tester connected to an endoscope that relates to a second modification of the present embodiment.

As shown in FIG. 5, in the present modification, in addition to the configuration of the first modification that is described above, the constant temperature portion 7 also includes a second temperature measurement portion 80 on a downstream side of the heater 72 in the air feed passage 71.

In such a configuration, for example, by subjecting the temperature of air that is blown from the constant temperature portion 7 to feedback control by the control portion 8 based on the relation between the target temperature Tt and a temperature T2 that is measured by the second temperature measurement portion 80, it is possible to subject the surface of the endoscope 2 to temperature control with higher accuracy.

Figure 6:
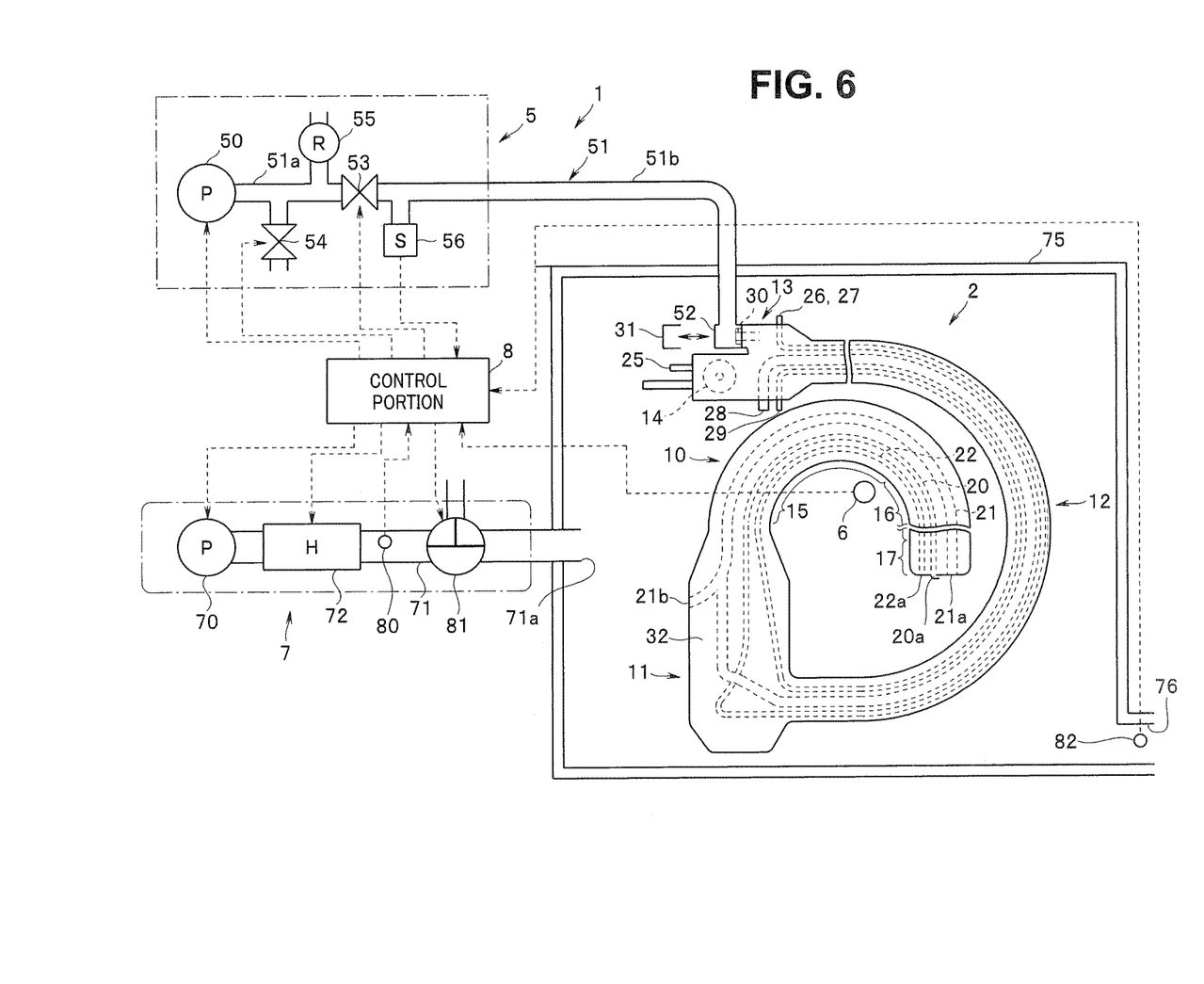
FIG. 6 is a block diagram illustrating a basic configuration of a leak tester that is connected to an endoscope according to a third modification of the second embodiment of the present invention.

Next, FIG. 6 is a block diagram illustrating a basic configuration of a leak tester connected to an endoscope that relates to a third modification of the present embodiment.

As shown in FIG. 6, in the present modification, in addition to the configuration of the second modification that is described above, the constant temperature portion 7 includes a three-way valve 81 on a downstream side of the second temperature measurement portion 80 in the air feed passage 71.

It is possible for the three-way valve 81 to, for example, selectively cause communication, cutting off of communication, or atmospheric release with respect to the air feed passage 71 at a region that is partway along the air feed passage 71 on a downstream side relative to the second temperature measurement portion 80.

In such a configuration, for example, by control of the three-way valve 81 by the control portion 8, a region that is partway along the air feed passage 71 can be opened to the atmosphere during a period until the temperature T2 that is measured by the second temperature measurement portion 80 reaches the target temperature Tt, and after the temperature T2 reaches the target temperature Tt, the ambient temperature inside the housing portion 75 can be efficiently controlled by switching the region that is partway along the air feed passage 71 to a communicating state.

In this case, for example, as shown in FIG. 6, it is also possible to provide a third temperature measurement portion 82 at the exhaust port 76 of the housing portion 75 and, when a temperature T3 that is measured by the third temperature measurement portion 82 reaches the target temperature Tt, determine that the overall ambient temperature inside the housing portion 75 has reached the target temperature Tt and stop the constant temperature portion 7 itself.

Figure 7:
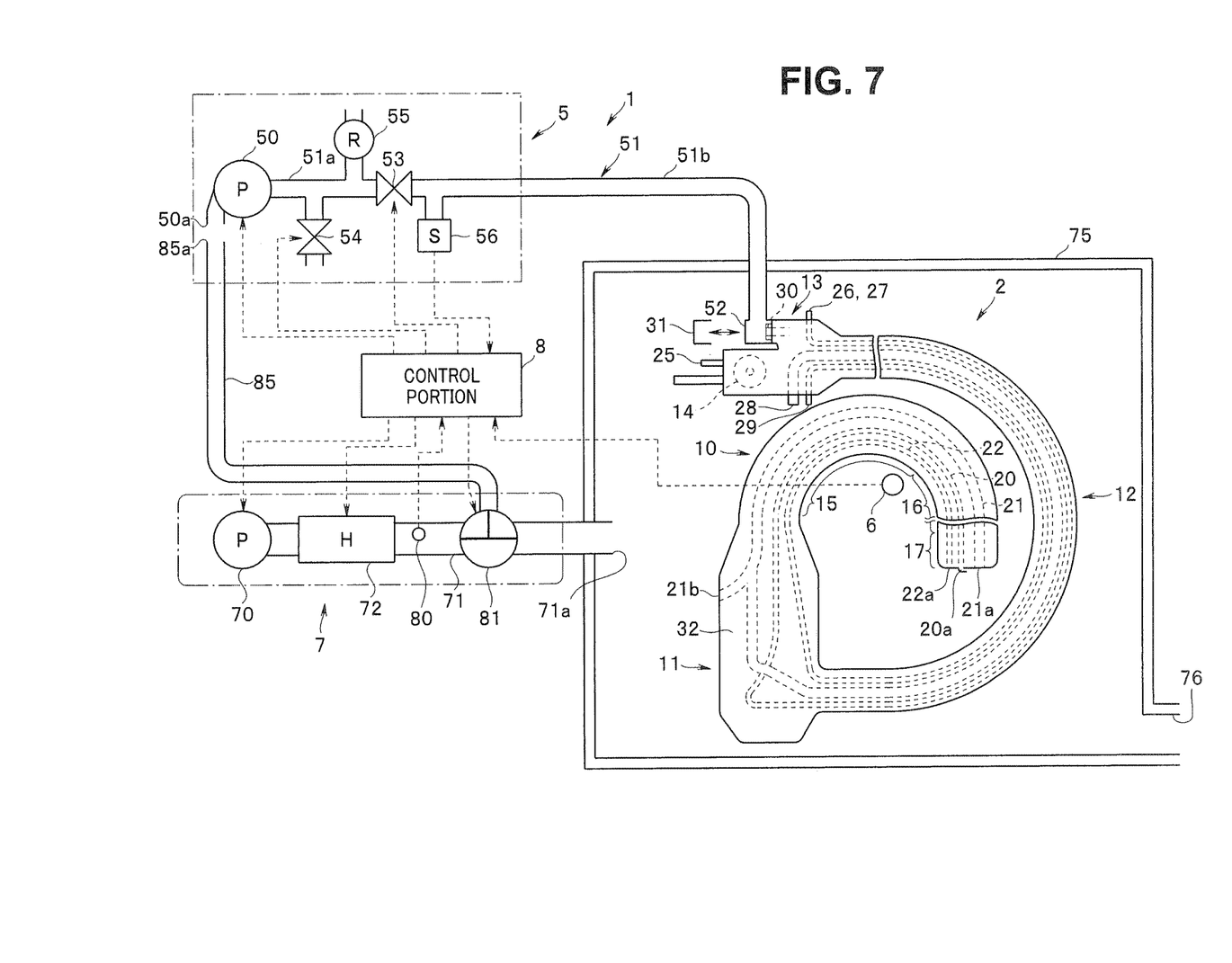
FIG. 7 is a block diagram illustrating a basic configuration of a leak tester that is connected to an endoscope according to a fourth modification of the second embodiment of the present invention.

Next, FIG. 7 is a block diagram illustrating a basic configuration of a leak tester connected to an endoscope that relates to a fourth modification of the present embodiment.

As shown in FIG. 7, in the present modification, in addition to the configuration of the second modification that is described above, the constant temperature portion 7 includes a branch passage 85 that branches from a downstream side of the second temperature measurement portion 80 in the air feed passage 71, and a three-way valve 81 that is interposed at a portion at which the branch passage 85 branches from the air feed passage 71.

The branch passage 85 is extended to the leak tester main body 5 side, and a second air blowing port 85a that opens at a downstream end of the branch passage 85 is disposed so as to face an intake port 50a of an air pump 50. That is, in the present modification, the air blowing port 71a (first air blowing port) that opens at the downstream end of the air feed passage 71 itself is oriented so as to be capable of blowing air toward the endoscope 2, and the second air blowing port 85a that opens at the downstream end of the branch passage 85 is oriented so as to be capable of blowing air toward the intake port 50a of the air pump 50.

The three-way valve 81, for example, is configured to be capable of selectively performing an operation to, on a downstream side relative to the second temperature measurement portion 80, allow communication with respect to only a region partway along the air feed passage 71, allow communication only between the heater 72 side of the air feed passage 71 and the branch passage 85, or allow communication with respect to the region partway along the air feed passage 71 and communication between the heater 72 side of the air feed passage 71 and the branch passage 85.

In such configuration, for example, by control of the three-way valve 81 by the control portion 8, during a period until the temperature T2 that is measured by the second temperature measurement portion 80 reaches the target temperature Tt, only the heater 72 side of the air feed passage 71 and the branch passage 85 are caused to communicate. Note that, at this time, the air pump 50 is placed in a stopped state by control of the control portion 8.

Thereafter, when the temperature T2 reaches the target temperature Tt, the region partway along the air feed passage 71 is placed in a communicating state and the heater 72 side of the air feed passage 71 and the branch passage 85 are placed in a communicating state, and the air pump 50 is driven. By this means, not only the ambient temperature of the endoscope 2, but also the temperature of air that is supplied into the empty space portion 32 inside the endoscope 2 can be controlled to the target temperature Tt, and thus the accuracy of a leak determination can be further improved.

Note that, although not illustrated in the drawings, a configuration may also be adopted in which, instead of the branch passage 85, a conduit is provided that guides air that is discharged from the exhaust port 76 of the housing portion 75 to the intake port 50a of the air pump 50, to thereby supply warm air that is discharged from the housing portion 75 to the air pump 50.

Figure 8:
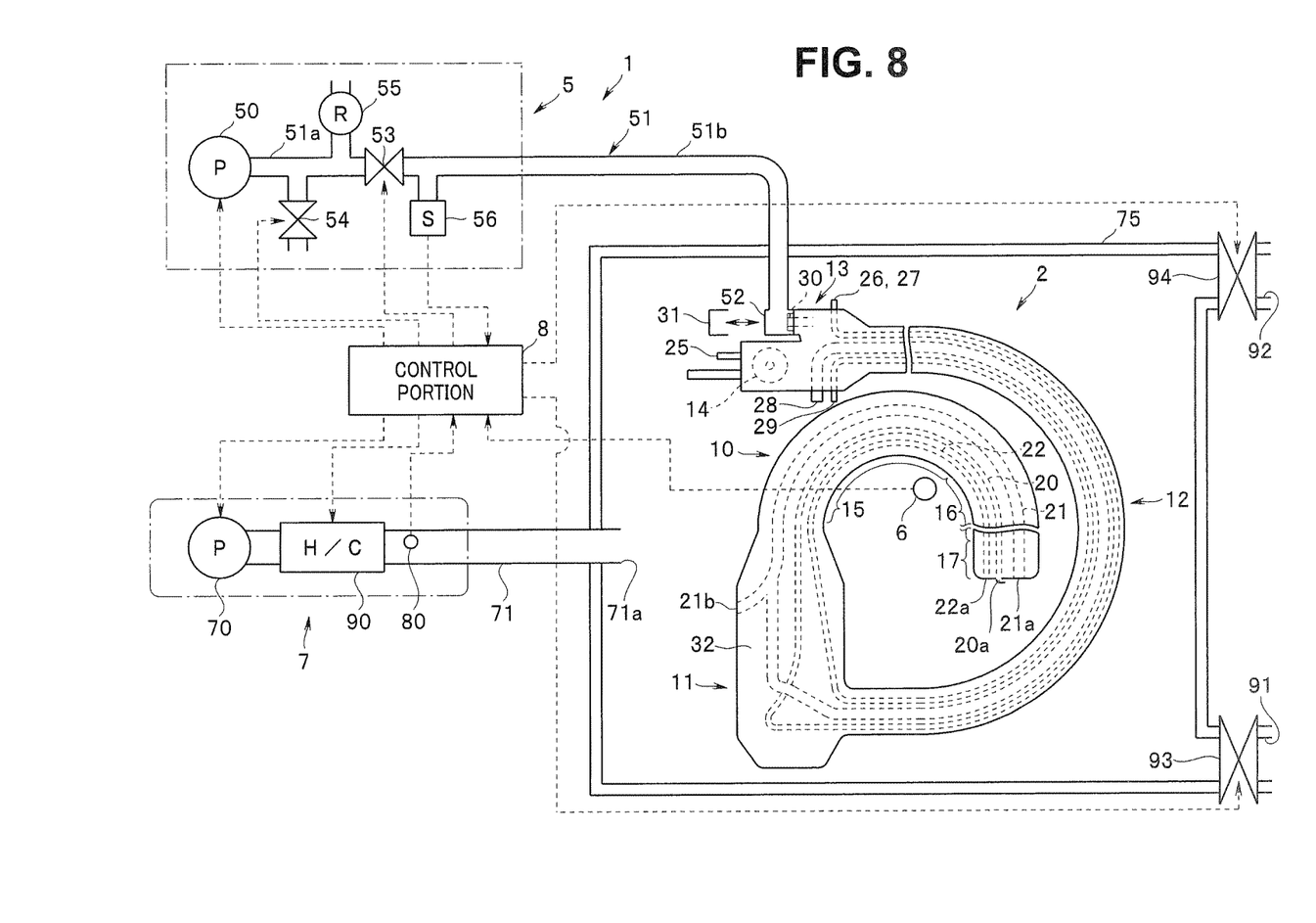
FIG. 8 is a block diagram illustrating a basic configuration of a leak tester that is connected to an endoscope according to a fifth modification of the second embodiment of the present invention.

Next, FIG. 8 is a block diagram illustrating a basic configuration of a leak tester connected to an endoscope, which relates to a fifth modification of the present embodiment.

As shown in FIG. 8, in the present modification, instead of the heater 72 shown in the second modification that is described above, the constant temperature portion 7 includes a Peltier element 90 as a heat source portion. That is, in the present modification, the constant temperature portion 7 is configured so that, at the time of performing a leak test, in a case where the surface temperature T of the endoscope 2 is higher than the ambient temperature, the constant temperature portion 7 can blow air that was heated by the Peltier element 90, while in a case where the surface temperature T of the endoscope 2 is lower than the ambient temperature, the constant temperature portion 7 can blow air from which heat was absorbed by the Peltier element 90.

Further, since not only warm air but also cold air can be efficiently accumulated inside the housing portion 75, a first exhaust port 91 that can be opened/closed by a first exhaust valve 93 is provided at a lower part of the housing portion 75, and a second exhaust port 92 that can be opened/closed by a second exhaust valve 94 is provided at an upper part of the housing portion 75.

According to the configuration, in a case where the ambient temperature is lower than the target temperature Tt, the control portion 8 performs heat generation control with respect to the Peltier element 90 (that is, causes the Peltier element 90 to act as a positive heat source portion), and supplies heated air into the housing portion 75. At this time, in order to efficiently accumulate warm air inside the housing portion 75, the control portion 8 controls to open the first exhaust valve 93 and also controls to close the second exhaust valve 94.

In contrast, in a case where the ambient temperature is higher than the target temperature Tt, the control portion 8 performs heat absorption control with respect to the Peltier element 90 (that is, causes the Peltier element 90 to act as a negative heat source portion), and supplies cooled air into the housing portion 75. At this time, in order to efficiently accumulate cold air inside the housing portion 75, the control portion 8 controls to close the first exhaust valve 93 and also controls to open the second exhaust valve 94.

According to such a modification, by using the Peltier element 90 as a heat source portion, an automatic leak determination can be accurately performed in a short time with respect to not only the endoscope 2 that became a high temperature as the result of use, but also with respect to the endoscope 2 that was brought in from a cold place or the like.

Figure 9:
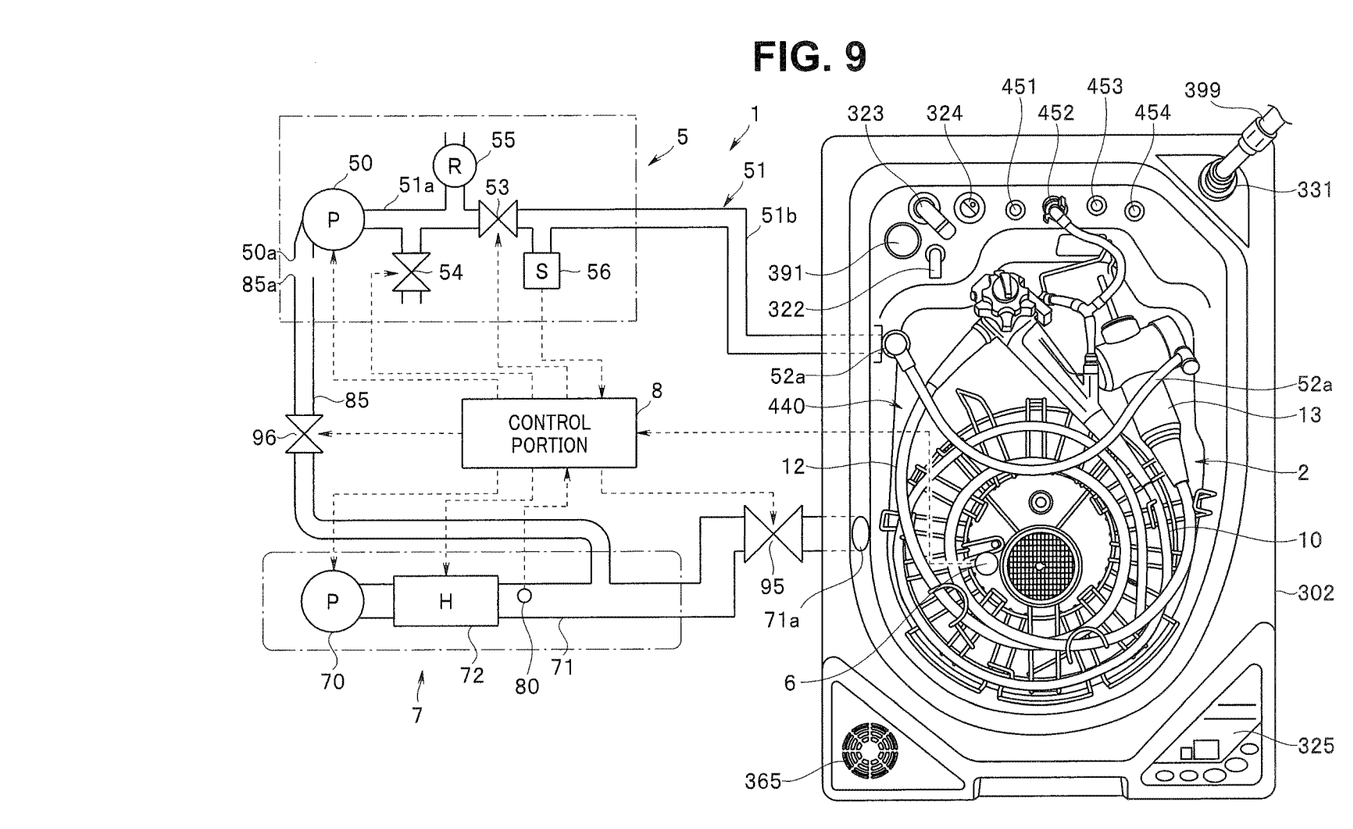
FIG. 9 is a block diagram illustrating a basic configuration of a leak tester that is connected to an endoscope inside an endoscope reprocessor according to a third embodiment of the present invention.
Figure 10:
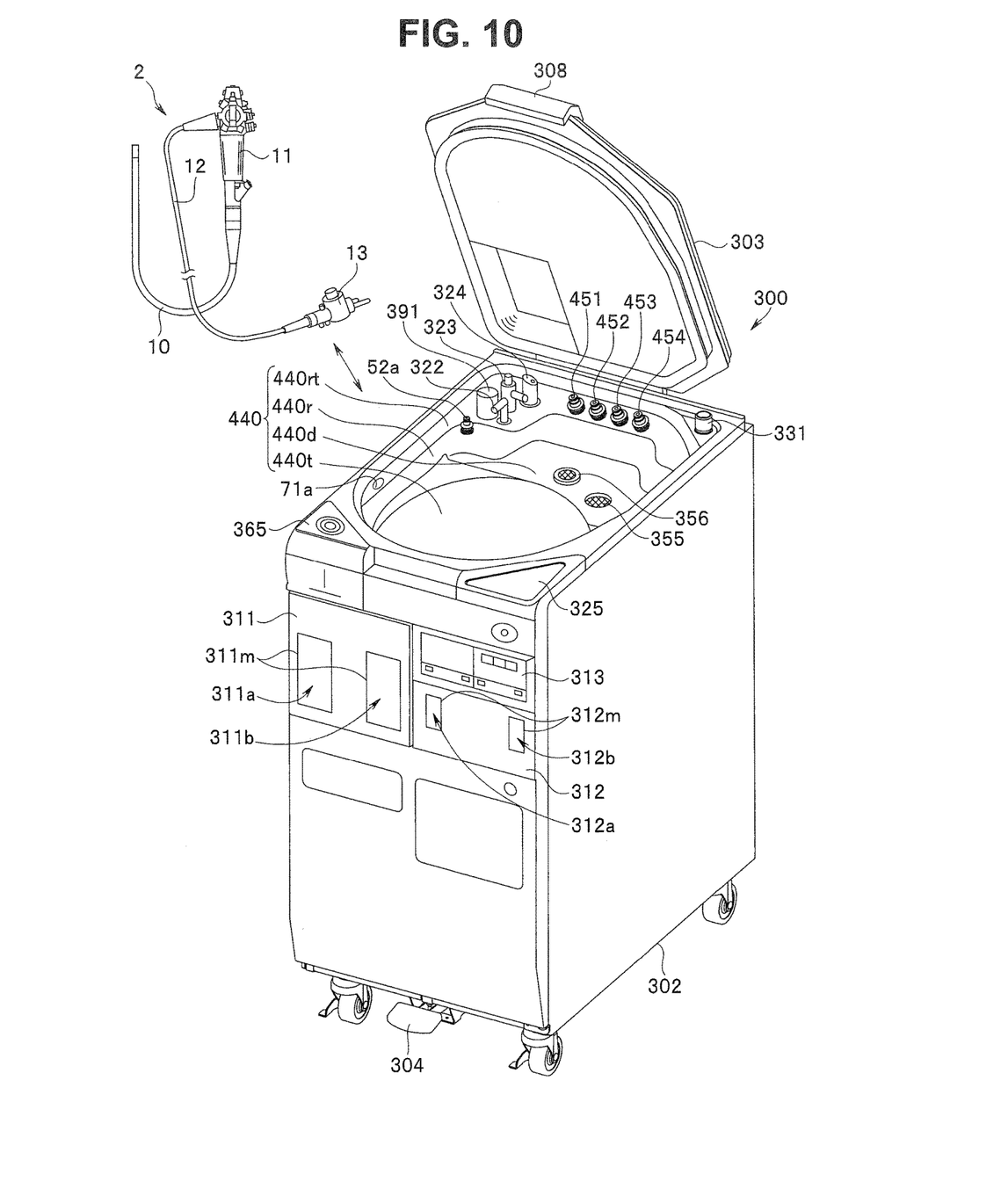
FIG. 10 is a perspective view of the endoscope reprocessor according to the third embodiment of the present invention.

Next, FIGS. 9 and 10 relate to a third embodiment of the present invention. FIG. 9 is a block diagram illustrating a basic configuration of a leak tester connected to an endoscope inside an endoscope reprocessor. FIG. 10 is a perspective view of the endoscope reprocessor. An endoscope reprocessor is an apparatus that performs a regeneration treatment on an endoscope. The regeneration treatment referred to here is not particularly limited, and may be any one of, or a combination of any two or more of: a rinsing treatment using water, a cleaning treatment that removes dirt such as organic matter, a disinfecting treatment that nullifies predetermined microorganisms, and a sterilization treatment that eliminates or kills all microorganisms.

Note that the present embodiment is described with respect to an example of a case of applying the leak tester 1 to an endoscope reprocessor 300. More specifically, in the present embodiment, for example, the leak tester 1 that has substantially the same configuration as the configuration illustrated in the above-described fourth modification of the second embodiment is applied to the endoscope reprocessor 300. Accordingly, components that are the same as components in the above-described embodiments are denoted by the same reference numerals and descriptions of such components are omitted hereunder.

The endoscope reprocessor 300 illustrated in FIG. 10 is an apparatus for cleaning and disinfecting the endoscope 2 after use, in which a principal portion is constituted by an apparatus main body 302 and a top cover 303 that is connected by, for example, a hinge (not shown), to the upper part of the apparatus main body 302 so as to be openable/closable.

In a state in which the top cover 303 is closed on the apparatus main body 302, the apparatus main body 302 and the top cover 303 are fixed, for example, by a latch 308 that is arranged at a position at which the apparatus main body 302 and the top cover 303 face each other.

A cleanser/alcohol tray 311 is arranged at the upper part of a left half portion, for example, on the front face in FIG. 10 of the apparatus main body 302 so as to be capable of being drawn out in the forward direction from the apparatus main body 302, the front face being a side which the operator approaches.

The cleanser/alcohol tray 311 houses a cleanser tank 311a in which a cleaning agent that is a liquid that is used when cleaning the endoscope 2 is stored, and an alcohol tank 311b in which alcohol that is a liquid that is used when drying the endoscope 2 after cleaning/disinfecting is stored. The cleanser/alcohol tray 311 can be drawn out from the apparatus main body 302 so that the liquids can be replenished to a prescribed level in the respective tanks 311a and 311b.

Note that the cleanser/alcohol tray 311 is provided with two window portions 311m through which the operator can confirm the remaining amounts of the cleaning agent and alcohol filled in the respective tanks 311a and 311b.

In addition, a disinfectant solution tray 312 is arranged at the upper part of a right half portion, for example, on the front face of the apparatus main body 302 so as to be capable of being drawn out in the forward direction from the apparatus main body 302. Two chemical bottles 312a and 312b into which a disinfectant solution such as an aqueous peracetic acid solution is filled that are to be used when disinfecting the endoscope 2 are housed in the disinfectant solution tray 312. The disinfectant solution tray 312 can be drawn out from the apparatus main body 302 so that the two chemical bottles 312a and 312b can be set as prescribed. Note that the disinfectant solution tray 312 is provided with two window portions 312m through which the operator can confirm the remaining amount of the disinfectant solution filled in the respective chemical bottles 312a and 312b. Note that, in the case of an endoscope reprocessor that performs a sterilization treatment on an endoscope, the chemical bottles 312a and 312b in which a sterilizing solution is filled can be disposed in the disinfectant solution tray 312. An aqueous peracetic acid solution may be mentioned as an example of the sterilizing solution.

In addition, a sub-operation panel 313 which includes instruction buttons for displaying a cleaning/disinfecting time period and for heating the disinfectant solution is arranged above the disinfectant solution tray 312 on the front face of the apparatus main body 302.

Furthermore, a pedal switch 304 is arranged at a lower part on the front face in FIG. 10 of the apparatus main body 302. The pedal switch 304 is provided for causing the top cover 303 that is closed on the upper part of the apparatus main body 302 to open in the upward direction of the apparatus main body 302 when the operator steps on the pedal switch 304.

Further, the apparatus main body 302 includes a main operation panel 325 on the upper surface of the apparatus main body 302 at, for example, a position that is close to the right end on the front face side which the operator approaches. The main operation panel 325 includes setting switches such as a switch for starting a cleaning/disinfecting operation of the apparatus main body 302 and a cleaning/disinfecting mode selection switch. The apparatus main body 302 also includes, on the upper surface of the apparatus main body 302, a receiving portion 365 that is provided at a position close to the left end on the front face side which the operator approaches. The receiving portion 365 is configured by, for example, an RFID that receives information from the endoscope 2 when the endoscope 2 is brought close to the RFID.

In addition, a water supply hose connection port 331 is arranged on the upper surface of the apparatus main body 302 so as to be located on a rear face side that opposes the front face which the operator approaches. The water supply hose connection port 331 is connected to a water supply hose 399 which is connected to a water tap for supplying tap water to the apparatus main body 302. Note that a mesh filter that filters the tap water may be arranged in the water supply hose connection port 331.

Furthermore, a treatment tank 440 as a housing portion which can house the endoscope 2 and which has an endoscope housing opening that is opened and closed by the top cover 303 is provided at a substantially center portion of the upper surface of the apparatus main body 302.

The treatment tank 440 is configured by: a first tank main body 440*t* that is located on the front face side which the operator approaches; a second tank main body 440*d* that is located at a position on the rear side relative to the first tank main body 440*t* and whose bottom surface is at a lower position than that of the first tank main body 440*t*; and a terrace portion 440*r* that is provided around the periphery so as to be continuous with the outer peripheral edge of the endoscope housing opening of the first tank main body 440*t* and the second tank main body 440*d*.

When the endoscope 2 is to be cleaned/disinfected, the endoscope 2 can be housed in the first tank main body 440*t* and the second tank main body 440*d*. Note that the insertion portion 10 and the universal cord 12 of the endoscope 2 are wound up and housed in the first tank main body 440*t*, and the operation portion 11 and the connector portion 13 of the endoscope 2 are housed in the second tank main body 440*d*.

On the bottom surface of the second tank main body 440*d* are provided: a drainage port 355 for draining from the first tank main body 440*t* and the second tank main body 440*d* a cleaning solution, water, alcohol, a disinfectant solution or the like that is supplied to the first tank main body 440*t* and the second tank main body 440*d*; and a circulation port 356 for supplying the cleaning liquid, water, disinfectant solution or the like that was supplied to the first tank main body 440*t* and the second tank main body 440*d* to respective conduits provided inside the endoscope 2 or for resupplying the aforementioned liquids from a water-supply circulation nozzle 324, described later, to the first tank main body 440*t* and the second tank main body 440*d* through a mesh filter or the like. Note that a mesh filter that filters the cleaning liquid and the like may be provided in the circulation port 356.

A cleanser nozzle 322 and a disinfectant solution nozzle 323 are provided in a terrace face 440*rt* of the terrace portion 440*r*. The cleanser nozzle 322 is used for supplying the cleaning agent that is diluted to a predetermined concentration with tap water from the cleanser tank 311*a* to the first tank main body 440*t* and the second tank main body 440*d*. The disinfectant solution nozzle 323 is used for supplying the disinfectant solution to the first tank main body 440*t* and the second tank main body 440*d*.

The water-supply circulation nozzle 324 and a float switch 391 are also provided on the terrace face 440*rt*. The water-supply circulation nozzle 324 is used for supplying water to the first tank main body 440*t* and the second tank main body 440*d* or for resupplying the cleaning liquid, water, disinfectant solution or the like which are sucked through the circulation port 356 to the first tank main body 440*t* and the second tank main body 440*d*. The float switch 391 detects an abnormal level of the cleaning liquid, water, disinfectant solution or the like that is supplied to the first tank main body 440*t* and the second tank main body 440*d*.

In addition, connectors 451 to 454 for supplying the cleaning liquid, water, alcohol, disinfectant solution or air or the like through cleaning tubes to various conduits provided inside the endoscope 2 are provided on the terrace face 440*rt*.

In the endoscope reprocessor 300 having the above-described configuration, an endoscope connection portion 52*a* as a connection portion that communicates with downstream-side conduit portion 51*b* of the leak tester main body 5 is provided on the terrace portion 440*r*. The endoscope connection portion 52*a* is configured to be capable of communicating with the inside (empty space portion 32) of the endoscope 2 through the connection conduit 52*b*.

Further, the air blowing port 71*a* of the air feed passage 71 is opened in the terrace portion 440*r*. Note that, in the present embodiment, instead of the three-way valve 81, control valves 95 and 96 that are individually controlled to open and close by the control portion 8 are interposed partway along the air feed passage 71 and partway along the branch passage 85, respectively.

According to the embodiment, it is enabled to perform respective processes of a leak test, cleaning, disinfecting and the like with respect to the endoscope 2 as a series of processes in the single endoscope reprocessor 300.

It is to be understood that the present invention is not limited to the respective embodiments described above, and various modifications and changes are possible, and such changes and modifications are also within the technical scope of the present invention. For example, naturally the configurations illustrated in the respective embodiments and modifications described above may be appropriately combined.

Further, although the foregoing embodiments and modifications are described taking an endoscope as an example of an object of a leak test, the present invention is not limited thereto, and naturally it is also possible to apply the present invention to a leak test for various other kinds of devices or to a leak test in various kinds of manufacturing processes.

A tire or the like may be mentioned as a specific example of the object.

What is claimed is:

1. A leak tester, comprising:
a connection portion that is communicably connected to inside of an endoscope;
an air feeding portion configured to feed a gas into the endoscope through the connection portion;
an internal pressure measurement portion configured to measure an internal pressure of the endoscope;
a temperature measurement portion configured to measure a surface temperature of the endoscope;
a constant temperature portion configured to supply energy toward a surface of the endoscope; and
a control portion that is connected to the air feeding portion, the internal pressure measurement portion, the temperature measurement portion, and the constant temperature portion, and is configured to set as a target temperature a surface temperature of the endoscope that is measured by the temperature measurement portion before driving of the internal pressure measurement portion and the air feeding portion, and
to control the constant temperature portion so that the constant temperature portion causes a change in the surface temperature of the endoscope to be a temperature within a predetermined range from the target temperature at least during driving of the internal pressure measurement portion.

2. The leak tester according to claim 1, wherein
the constant temperature portion includes a heat source portion configured to regulate a temperature of the gas, and
the energy is supplied to the endoscope through the gas whose temperature is regulated.

3. The leak tester according to claim 1, wherein
the constant temperature portion includes a heat source portion configured to regulate a temperature of the gas, and an air blowing portion configured to blow the gas whose temperature is regulated toward the endoscope, and
the energy is supplied to the endoscope through the gas that is blown.

4. The leak tester according to claim 3, wherein
the air feeding portion includes an intake port configured to take in the gas, and
the air blowing portion includes a first air blowing port configured to blow the gas whose temperature is regulated toward the endoscope, and a second air blowing port configured to blow the gas whose temperature is regulated toward the intake port.

5. The leak tester according to claim 1, comprising:
a housing portion configured to house the endoscope,
wherein the constant temperature portion is configured to control a temperature of a gas inside the housing portion to a same temperature as the surface temperature of the endoscope at a predetermined timing when the endoscope is housed in the housing portion, or to a temperature within a predetermined range obtained by adding and subtracting a predetermined temperature to and from the surface temperature.

6. An endoscope reprocessor, comprising:
a leak tester according to claim 5, wherein:
the connection portion includes an endoscope connection portion configured to communicate with inside of the endoscope, and
the housing portion is a treatment tank configured to house the endoscope.

7. A leak tester, comprising:
a connection portion that is communicably connected to inside of an object;
an air feeding portion configured to feed a gas into the object through the connection portion;
an internal pressure measurement portion configured to measure an internal pressure of the object;
a temperature measurement portion configured to measure a surface temperature of the object;
a constant temperature portion configured to supply energy toward a surface of the object; and
a control portion that is connected to the air feeding portion, the internal pressure measurement portion, the temperature measurement portion, and the constant temperature portion, and is configured to set as a target temperature a surface temperature of the object that is measured by the temperature measurement portion before driving of the internal pressure measurement portion and the air feeding portion, and
to control the constant temperature portion so that the constant temperature portion causes a change in the surface temperature of the object to be a temperature within a predetermined range from the target temperature at least during driving of the internal pressure measurement portion,
wherein the energy is far infrared rays, and
the constant temperature portion includes a far-infrared ray irradiation portion configured to irradiate far infrared rays.

8. The leak tester according to claim 7, wherein the object is an endoscope.

* * * * *